(12) United States Patent
Koehler et al.

(10) Patent No.: US 11,011,261 B2
(45) Date of Patent: May 18, 2021

(54) DEVICE FOR GENERATING PROTOCOL DATA FOR AN INJECTION PEN

(71) Applicant: Roche Diabetes Care, Inc., Indianapolis, IN (US)

(72) Inventors: Matthias Koehler, Laudenbach (DE); Uwe Kraemer, Ilvesheim (DE); Timm Wiedemann, Mannheim (DE); Marcus Vetter, Dossenheim (DE)

( * ) Notice: Subject to any disclaimer, the term of this patent is extended or adjusted under 35 U.S.C. 154(b) by 0 days.

(21) Appl. No.: 16/318,724

(22) PCT Filed: Jul. 18, 2017

(86) PCT No.: PCT/EP2017/068160
§ 371 (c)(1),
(2) Date: Jan. 18, 2019

(87) PCT Pub. No.: WO2018/015401
PCT Pub. Date: Jan. 25, 2018

(65) Prior Publication Data
US 2019/0244702 A1  Aug. 8, 2019

(30) Foreign Application Priority Data

Jul. 18, 2016 (EP) ..................... 16180031
Mar. 8, 2017 (EP) ..................... 17159954

(51) Int. Cl.
*G16H 20/17* (2018.01)
*A61M 5/315* (2006.01)
*G16H 40/63* (2018.01)

(52) U.S. Cl.
CPC ........ *G16H 20/17* (2018.01); *A61M 5/31568* (2013.01); *G16H 40/63* (2018.01);
(Continued)

(58) Field of Classification Search
CPC ... G16H 20/17; G16H 40/63; A61M 5/31568; A61M 5/3155; A61M 5/32; A61M 5/345; G01R 31/2858
See application file for complete search history.

(56) References Cited

U.S. PATENT DOCUMENTS 6,122,538 A * 9/2000 Sliwa, Jr. ............... A61B 8/00
324/207.14
2011/0313349 A1* 12/2011 Krulevitch ............ A61M 5/315
604/65
(Continued)

FOREIGN PATENT DOCUMENTS

EP  3188061 A  7/2017
KR  101037001 B1 *  5/2011 ............ G01C 19/66
(Continued)

OTHER PUBLICATIONS

Office Action in related EP17748420.1 dated Nov. 27, 2020.

*Primary Examiner* — Jermele M Hollington
*Assistant Examiner* — Taqi R Nasir
(74) *Attorney, Agent, or Firm* — Woodard, Emhardt, Henry, Reeves & Wagner, LLP

(57) ABSTRACT

The invention concerns a device (1) for generating protocol data for an injection pen (2). The device (1) comprises a motion sensing unit (13) including one or more of a gyroscope and an accelerometer in order to generate one or more of a gyro signal and an acceleration signal. The device comprises a signal processing unit (14) which implements an analyser which is configured to analyse one or more of the gyro signal and the acceleration signal and to generate protocol data reflecting an adjusted dosage of a medicament. Optionally, the analyser is configured to generate protocol data reflecting delivery of the adjusted dosage of the medicament.

21 Claims, 8 Drawing Sheets

(52) U.S. Cl.
CPC ... *A61M 5/3155* (2013.01); *A61M 2205/0244* (2013.01); *A61M 2205/332* (2013.01); *A61M 2205/3327* (2013.01); *A61M 2205/3365* (2013.01); *A61M 2205/3569* (2013.01); *A61M 2205/3584* (2013.01); *A61M 2205/50* (2013.01); *A61M 2205/502* (2013.01); *A61M 2205/52* (2013.01); *A61M 2205/581* (2013.01); *A61M 2205/6009* (2013.01); *A61M 2205/702* (2013.01); *A61M 2205/8206* (2013.01); *A61M 2205/8212* (2013.01)

(56) References Cited

U.S. PATENT DOCUMENTS

| | | | | |
|---|---|---|---|---|
| 2014/0207099 | A1* | 7/2014 | Nagar | A61M 5/50 604/503 |
| 2014/0257141 | A1* | 9/2014 | Giuffrida | A61B 5/1124 600/595 |
| 2014/0316305 | A1* | 10/2014 | Venkatraman | A61B 5/681 600/595 |
| 2016/0030683 | A1* | 2/2016 | Taylor | A61M 5/168 604/151 |
| 2018/0311445 | A1* | 11/2018 | Boggild-Damkvist | G16H 20/17 |

FOREIGN PATENT DOCUMENTS

| | | |
|---|---|---|
| WO | WO 2010/098927 | 9/2010 |
| WO | WO 2015/136513 | 9/2015 |
| WO | WO 2017/132577 | 8/2017 |

* cited by examiner

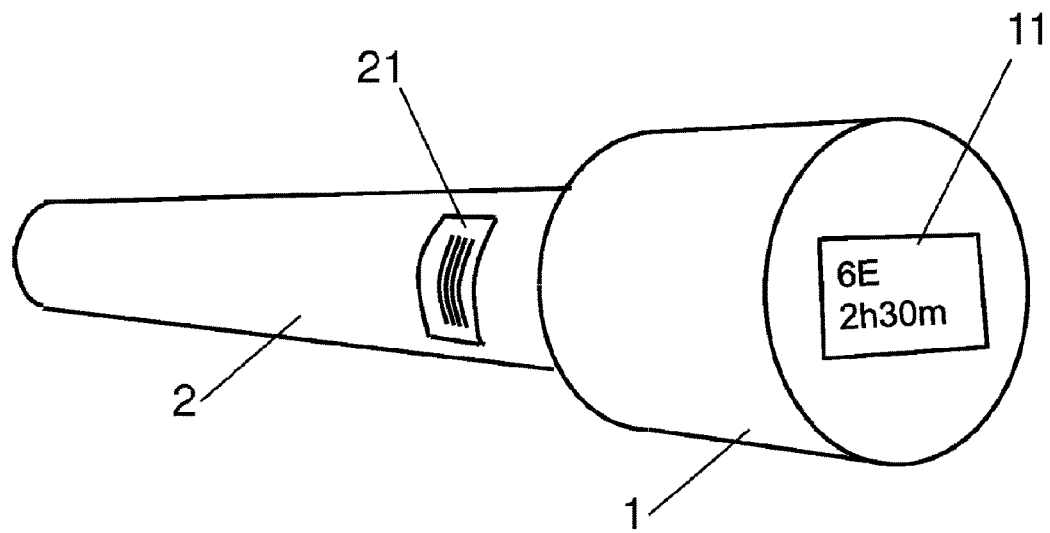
Fig. 1
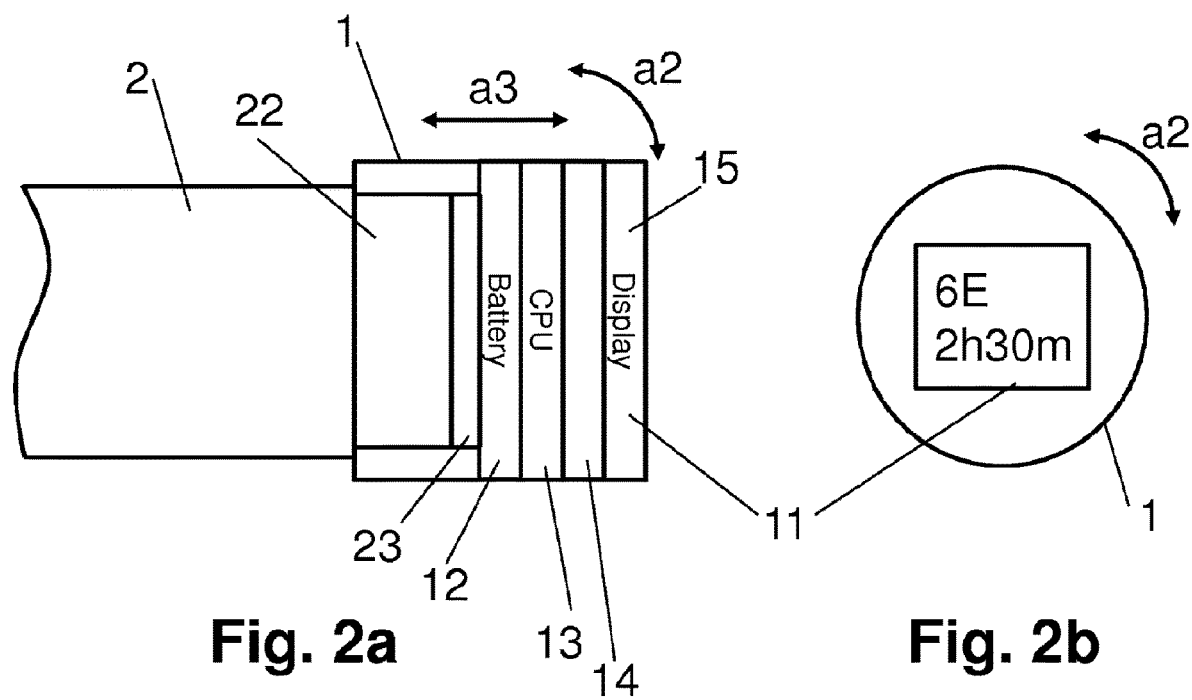
Fig. 2a  Fig. 2b

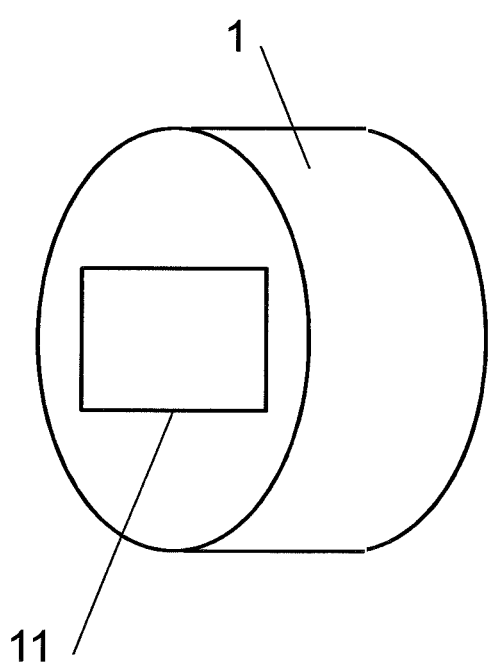
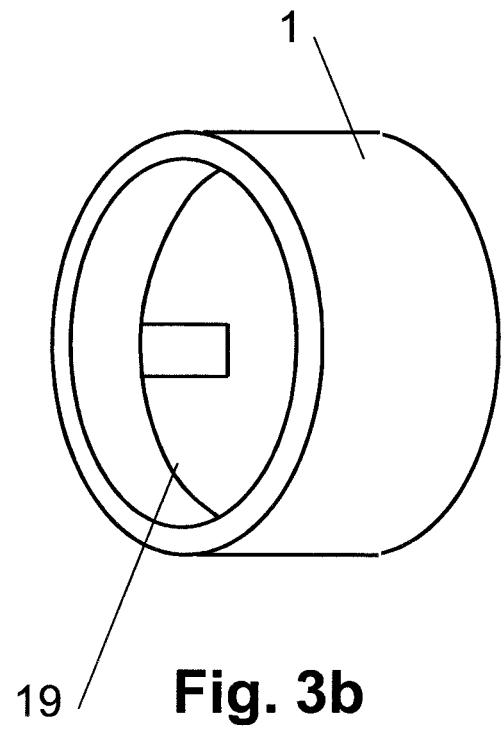
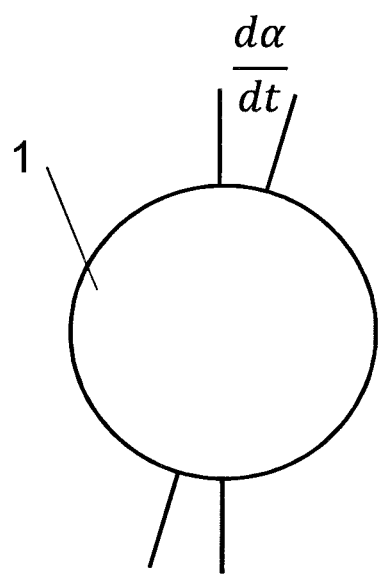

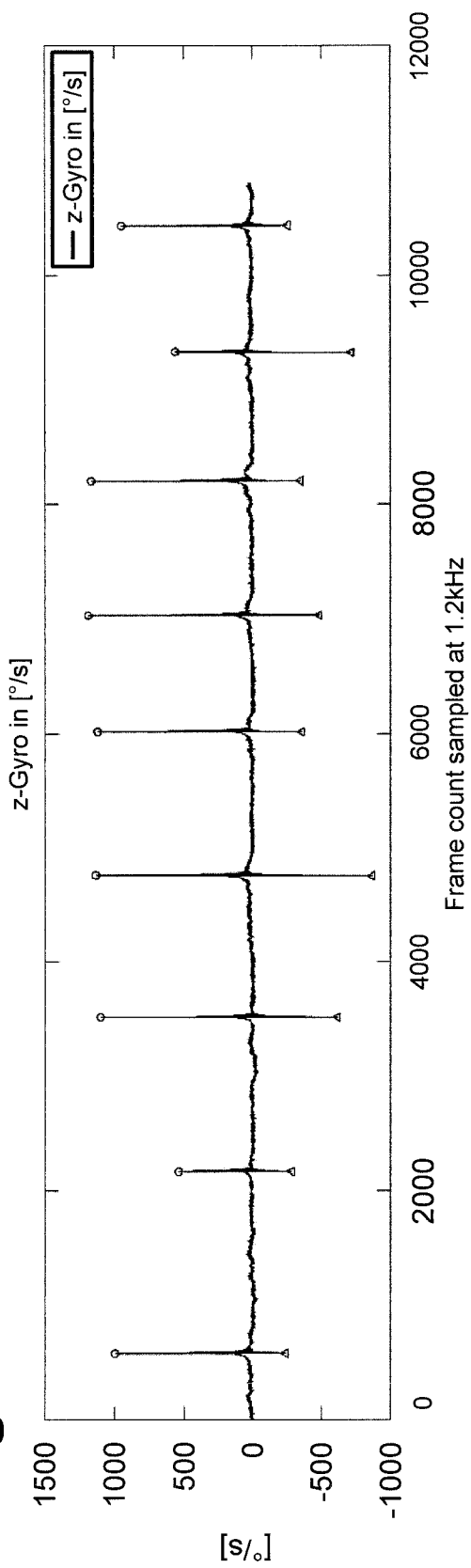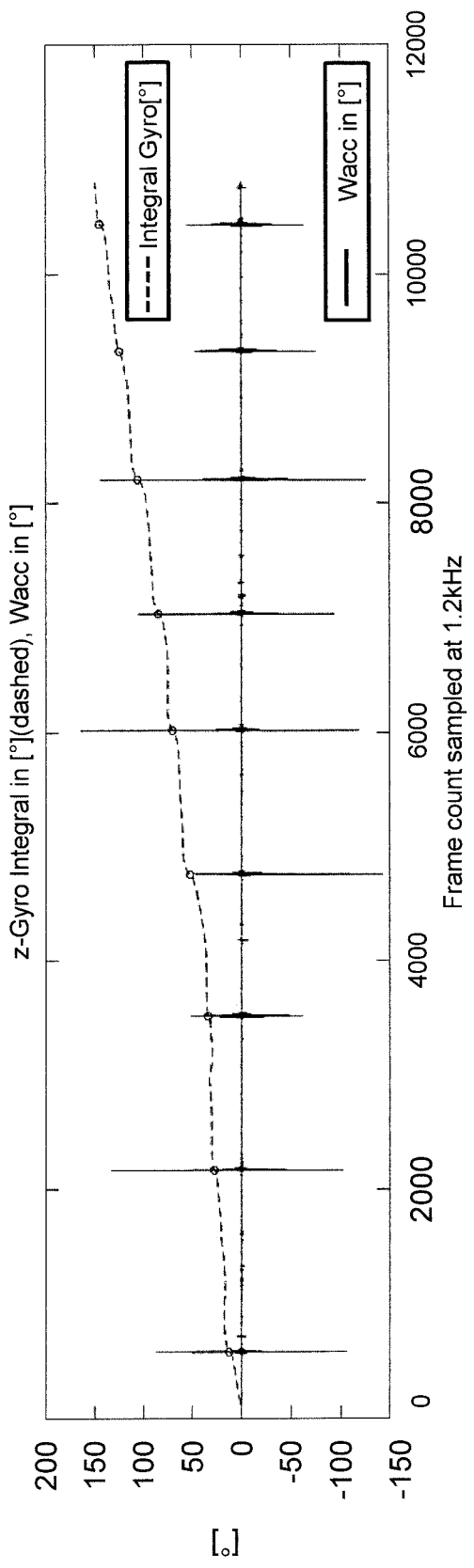

DEVICE FOR GENERATING PROTOCOL DATA FOR AN INJECTION PEN

FIELD OF THE INVENTION

The present invention relates to a device for generating protocol data for an injection pen. Moreover, the invention relates to an injection pen comprising the device for generating protocol data for an injection pen.

BACKGROUND ART

Many patients need therapies based on individualized injections of medicaments. For example, patients suffering from diabetes often require individualized injections of insulin multiple times every day. Medicaments such as insulin are delivered in doses that normally correspond to individual characteristics of a patient, such as body mass, age, blood sugar level, gender, etc, and to the current behaviour of the patient, such as the intention to have a meal.

Multiple daily injections (MDI) using an injection pen is a widely applied method in therapy, such as in insulinotherapy. Injection pens include an injection needle for delivery of the medicament from a reservoir of the injection pen into the patient. Injection pens further include a dosing mechanism for adjusting a dosage of the medicament and an activation mechanism for delivery of the adjusted dosage of the medicament into the patient.

Usually, injection pens are purely mechanical devices. An injection pen usually accommodates multiple dosages of the medicament so that a patient can use the same injection pen multiple times. Typically, the reservoir of the injection pen can be replaced.

Delivering an individualized dosage of a medicament using an injection pen includes performing a sequence of several steps with the injection pen, such as, for example, the following steps. In a first step, the patient adjusts the dosage of the medicament to be delivered by manipulating a dosing mechanism of the injection pen, such as by rotating by an appropriate angle a dosing adjustment wheel of the injection pen. After having adjusted the dosage of the medicament, in a second step, the patient inserts the injection needle into the body by penetrating the skin with the injection needle. After having inserted the injection needle into the body, in a third step, the patient initiates the delivery of the adjusted dosage of the medicament by manipulating the activation mechanism, such as by pressing a delivery push-button of the injection pen. After having initiated the delivery of the dosage of the medicament, in a fourth step, the patient waits for a while in order to avoid leak out of the medicament. After having waited for a while, in fifth step, the patient retracts the injection pen. After having retracted the injection pen, in a sixth step, the patient replaces the injection needle. After having replaced the injection needle, in a seventh step, the patient puts away the injection pen.

MDI patients have to carefully record protocol data about each injection of the medicament. Protocol data typically includes the dosage of the injection and the time of the injection. On the basis of protocol data, time and/or dosage of future injections can be determined. Protocol data is kept in a diary. Often, protocol data is manually recorded in a diary book or manually entered into a diary of a portable electronic device, such as a smartphone, a personal medical assistant, etc. The portable electronic device can be configured to analyse the protocol data and to inform the patient about the time and/or dosage of future injections, for example about the need of a further injection after the lapse of a time period or in case the patient is approaching the time of day when the patient usually eats a meal. The portable electronic device can be configured to inform the patient about the need of a further injection by generating an alarm, such as an optical alarm, an acoustical alarm, a vibration etc.

For many patients and/or in many situations, it is difficult to correctly and consistently update protocol data of each injection. For example, the portable electronic device may generate an alarm signalling that an injection is required when the patient is in a business meeting, in a traffic jam, or otherwise averted. In such situations, the patient usually delays the injection. However, after the delay and after having performed the injection, the patient may forget to update correctly the time of the injection. In another scenario, it may happen that the patient injects an incorrect dosage of the medicament, for example because the patient incorrectly adjusts the dosage or because the patient retracts the injection pen too early. In such situations, it may happen that the patient is not even aware that the protocol data needs to be adjusted. Moreover, even if the patient is aware of the incorrect dosage, it may happen that the patient forgets to adjust protocol data accordingly.

Poor management of individualized injections of medicaments can lead to serious and potentially life threatening complications. An accidental double insulin injection may result into a hypoglycaemic coma requiring hospitalization of the patient.

Several systems on the market allow basic logging functionality for MDI patients. For example, clip on adapters for an injection pen are available which determine and display the time since last injection. Replacement caps allow entering of bolus dosage.

WO2010/112575 relates to an arrangement for administering insulin or other medicines from a cartridge. A dosing knob enables setting and administering of a dose. The arrangement includes means for determining a set dose. The means for determining a set dose can include electrical contacts or magnetic elements which produce on the basis of a relative interaction of corresponding electrical contacts or magnetic elements an electrical signal in accordance to the rotation of the dosing knob. Data reflecting a set dose can be transmitted to a central data processing system.

US2016/0030683 discloses smart sensors that can be coupled to or retrofitted onto injection pen injectors. The smart sensors improve tracking of drug self-administration and stop medication errors that occur primarily through self or automated injection, e.g. due to incorrect or incomplete dosing, excessive dose or rate, incorrect drug, or drug degradation. The smart sensor can be in-line with respect to a drug delivery system's path of delivery. The pen can have a needle adapter that includes the smart sensor. Quickconnect interlocking means allow for coupling and decoupling of the components. The smart sensor is capable of wirelessly communicating with a portable user interface. The sensor can be a fluid detection sensor being in contact with the fluid. The sensor can use impedance spectroscopy. Other sensing techniques can include optical, electrical, mechanical, thermal and/or rheological techniques.

EP2427236A2 discloses a medication injection supervisor device comprising a sensor to detect an injection automatically. The sensor includes a micro switch or a micro optics subsystem. Usage data is detected. Usage data includes time of injection. Dosage of an injection is recorded. A display is included to display injection data.

WO2012001493A2 discloses a replaceable cap for a transdermal liquid dosing device such as an insulin pen. The cap includes an elongate hollow body with a first open end which can be placed over a front part of the dosing device and a second closed end opposite the first end. The cap body also includes a cavity which opens into the interior of the cap body and which houses a control unit which includes a timer unit, a switch mechanism that stands at least partially proud of the cavity so as to project into the interior of the body, and a timer display unit which displays time counted by the timer unit on an outer surface of the body of the cap. The switch mechanism is engaged by abutment of a surface of the front part of the dosing device when the cap is placed on the dosing device, and released when the cap is removed from the dosing device, the engagement and/or releasing of the switch mechanism causing the timer unit to reset after the elapse of a predetermined period of time, the time since the timer unit was last reset thereby indicating the time that has elapsed since the dosing device was last used.

DISCLOSURE OF THE INVENTION

It is an object of the present invention to provide a device for generating protocol data for an injection pen, which device does not have at least some of the disadvantages of the prior art. In particular, it is an object of the present invention to provide a device for generating protocol data for an injection pen, which device generates protocol data reflecting an adjusted dosage of a medicament and optionally a delivery of the adjusted dosage of the medicament.

According to the present invention, these objects are achieved through the features of the independent claims. In addition, further advantageous embodiments follow from the dependent claims and the description.

According to the present invention, the above-mentioned objects are particularly achieved in that the device comprises a motion sensing unit including a gyroscope and/or an accelerometer in order to generate a gyro signal and/or an acceleration signal. The device further comprises a signal processing unit which implements an analyser which is configured to analyse the gyro signal and/or the acceleration signal and to generate protocol data reflecting an adjusted dosage of a medicament and optionally to generate protocol data reflecting delivery of the adjusted dosage of the medicament. In particular, the analyser is implemented in the form of computer instructions (software) which are executed by the signal processing unit, in particular by a signal processor or a microprocessor. The gyroscope and/or the accelerometer can be implemented in the form of one or more MEMS devices (MEMS: micromechanical systems). The signal processing unit can comprise one or more microprocessors running a signal processing application for the analysis of the signals of the gyroscope and/or the accelerometer. The one or more microprocessors can further run a data generation application for the generation of protocol data based on the analysed signals of the gyroscope and/or the accelerometer. The motion sensing unit can be coupled to the signal processing unit via a communication interface such as an I2C serial interface (I2C: Inter-Integrated Circuit), SPI interface (SPI: Serial Peripheral Interface), etc. The device can be arranged with respect to the injection pen in a manner such that the motion sensing unit can register motions relating to a patient manipulating dosing adjustment means of the injection pen and/or delivery means of the injection pen, in order to enable the signal processing unit to analyse respective signals of the motion sensing unit.

In an embodiment, the analyser is adaptable to different types of injection pens. The gyro signal and/or the acceleration signal comprise particular features which are specific for a particular type of injection pens, such as an injection pen of a particular manufacturer, an injection pen of a particular model, etc. The device can therefore be used with various types of injection pens.

In an embodiment, the analyser is designed for a particular type of injection pens. The device can therefore be used only with a specific type of injection pens.

The analyser is configured to determine characteristic features in the gyro signal and the acceleration signal in order to determine the dosage which has been adjusted at the injection pen. The gyro signal and/or acceleration signal includes noise signals which distort the characteristic features. The analyser is configured to determine the adjusted dosage also in case of noise signals.

The analyser can have a trainable design. Training of the analyser can be performed at a production location of the device, wherein the analyser can be configured for a particular type of injection pen or for different types of injection pens. The analyser can be configured to provide a warning signal in case the device is used in connection with an unknown injection pen.

The analyser can include information which enables that the analyser can be adapted to different injection pens.

In an embodiment, the analyser is configured to adapt itself to the corresponding injection pen. For that purpose, the analyser can be configured to receive a type identifier of an injection pen, such as via NFC, barcode, mechanical, optical, etc. devices. Furthermore, the analyser can be configured to determine the corresponding injection pen on the basis of the gyro signal and/or acceleration signal, which may include signal components which are characteristic for a particular type of injection pens.

The analyser can be configured that only for particular types of injection pens generation of protocol data is performed.

In an embodiment, the device includes a universal part which can be used with different types of injection pens and an adapter part which is designed to adapt the universal part to a particular type of injection pens. The universal part can include the signal processing unit implementing the analyser. The adapter part can be designed for a particular type of injection pens. The adapter part can provide a type identifier of the injection pen, such as described above.

In an embodiment, the analyser is adaptable to an injection pen on the basis of a training sequence of a user. The user can perform a particular training sequence with the injection pen in order to adapt the analyser to the injection pen. Instructions to the user for performing the training sequence can be given to the user under control of the device respectively the analyser.

In an embodiment, the device further comprises a communication interface for transmitting generated protocol data to an external protocol data recording device. The communication interface can be coupled to the signal processing unit. Transmission of generated protocol data can be controlled by the analyser. The communication interface can include a wireless interface, such as an IR interface (IR: Infrared), a Bluetooth interface, a Bluetooth Low Energy interface, or a NFC interface (NFC: Near Field Communication). The communication interface can include a wired interface, such as an USB interface (USB: Universal Serial Bus). The external protocol data recording device can be configured to include a time stamp into protocol data upon receipt. Accordingly, protocol data does not only include the adjusted dosage of the medicament and delivery of the adjusted dosage, but also the time of delivery. The external protocol data recording device can be a smartphone, a CGM device (CGM: Continous Glucose Monitoring), a notebook computer, a desktop computer, etc.

In an embodiment, the analyser is configured to generate protocol data having included a time stamp. Accordingly, the protocol data does not only include the adjusted dosage of the medicament and delivery of the adjusted dosage, but also the time of delivery.

A time stamp as described herein can refer to a relative ticker or count. The time stamp can refer to an absolute time (real time clock) such as the UTC time (UTC: Coordinated Universal Time), a time zone, etc.

Thus, the protocol data can include the adjusted dosage and the time of delivery of the medicament. The time of delivery can be included into the protocol data either by the device itself, or by the external protocol data recording device receiving protocol data from the device.

In an embodiment, the device further comprises a mounting arrangement configured to detachably mount the device to the injection pen. The mounting arrangement can provide that the device can be mounted to the injection pen at a suitable location of the injection pen. The mounting arrangement can provide that the device can be mounted to commercially available injection pens having included means for adjusting dosage and delivery of a medicament. The device can have the form of a cap having included a mounting arrangement which is configured to mount the device to dosage adjusting means of the injection pen and/or to a delivery means of the injection pen. The device can be adapted to provide an interface between a patient and the means arranged at the injection pen for manipulating the injection pen.

In an embodiment, the device further comprises a user interface having a user output device and/or a user input device. The user interface can be coupled to the signal processing unit. The user interface can be controlled by the analyser. The user output device can include a display, a loudspeaker, one or more LEDs (LED: light-emitting diode), a vibrating alert device, etc. The user input device can include a touchscreen, one or more switches, a microphone, etc. The analyser can be configured to analyse one or more signals of the gyroscope and/or the accelerometer in order to determine user input, for example to determine a user gesture.

In an embodiment, the analyser is configured to analyse the gyro signal and/or the acceleration signal in order to determine an angular velocity and/or a derivative of the angular velocity of a dosing adjusting means of the injection pen and to generate protocol data on the basis of the angular velocity and/or the derivative of the angular velocity of the dosing adjusting means of the injection pen the device is configured to generate protocol data on the basis of an angular velocity and/or a derivative of the angular velocity of a dosing adjusting means of the injection pen. The device can be mounted to the dosing adjusting means of an insulin pen. The dosing adjusting means can comprise a selector dial comprising a snap locking mechanism, wherein the speed of rotation and/or the acceleration of rotation of the selector dial can be used for generating the gyro signal and/or the acceleration signal. Based on the gyro signal and/or the acceleration signal, the analyser can be configured to perform a pattern matching and/or a pattern recognition in order to determine the adjusted dosage. The analyser can be configured to analyse the gyro signal and/or the acceleration signal and to determine the number of dialled units and the direction of rotation. The analyser can be configured to sum up the number of dialled units and to take into account the direction of rotation in order to determine the adjusted dosage of the medicament.

A snap locking mechanism of the injection pen can be configured to produce clicks that are acoustically perceivable by the user of the injection pen. The perceived clicks can correspond to the dialled units. The analyser can be configured to analyse the gyro signal and/or the acceleration signal in order to detect these clicks and to count the number of clicks in order to determine the adjusted dosage of the medicament. The direction of rotation can be taken into account in order to determine the adjusted dosage of the medicament from the detected clicks. In a variant, the clicks can form the only basis for determining the adjusted dosage.

In an embodiment, the analyser includes information which relates the detected clicks to the adjusted dosage. Some injection pens have a mechanism which provide one click for the dosing of 0.5 U (Units). Other injection pens include a mechanism which provide one click for the dosing of 1 U (Units).

In an embodiment, the analyser implements a data ring buffer which receives the gyro signal and/or the acceleration signal and which provides data segments in accordance to a peak detection in the gyro signal and/or the acceleration signal. The peak detection enables that data segments are provided which possibly include features related to the adjustment of a dosage.

In an embodiment, for the analysis of the gyro signal and/or the acceleration signal, the analyser implements a signal vector which comprises one or more of the following components: an x-component of the gyro signal, a y-component of the gyro signal, a z-component of the gyro signal, a derivative with respect to time of an x-component of the gyro signal, a derivative with respect to time of an y-component of the gyro signal, a derivative with respect to time of an z-component of the gyro signal, an x-component of the acceleration signal, a y-component of the acceleration signal, a z-component of the acceleration signal, a derivative with respect to time of an x-component of the acceleration signal, a derivative with respect to time of an y-component of the acceleration signal, a derivative with respect to time of an z-component of the acceleration signal, a projection of the gyro signal, a peak position in the gyro signal, and a signal length of the gyro signal and/or the acceleration signal. These signal components have proven to be useful for the analysis of the gyro signal and/or the acceleration signal.

In an embodiment, for the analysis of the gyro signal and/or the acceleration signal, the analyser implements a feature calculation for one or more components of the gyro signal and/or the acceleration signal, wherein the feature calculation includes one or more of: the calculation of the absolute maximum value in a signal segment, the calculation of the sum of the values of a signal segment, the calculation of the sum from the start to an absolute maximum position of a signal segment, the calculation of the sum from an absolute maximum position to the end of a signal segment, the calculation of the sum from the start to a peak position of a signal segment, the calculation of the sum from a peak position to the end of a signal segment, the calculation of the difference between the maximum and the minimum of a signal segment, and the calculation of the difference between the absolute maximum and the mean of a signal segment. These features of a signal component have proven to be useful for the analysis of the gyro signal and/or the acceleration signal.

In an embodiment, for the analysis of the gyro signal and/or the acceleration signal, the analyser implements a classifier in the form of a random forest classifier and/or a support vector machine. These classifiers have proven to be useful for the analysis of the gyro signal and/or the acceleration signal.

In an embodiment, the analyser is configured to generate protocol data on the basis of an acceleration and/or a derivative of the acceleration of a delivery means of the injection pen. The device is coupled to the delivery means. The analyser can be configured to determine a linear velocity and/or a derivative of the linear velocity of the delivery means of the injection pen on the basis of the gyro signal and/or the acceleration signal. The derivative can be determined with respect to time. The delivery means can comprise a push-button for activating delivery of the medicament, wherein the push speed and/or the acceleration of the push speed can be used for generating the gyro signal and/or the acceleration signal. Based on the gyro signal and/or the acceleration signal, a pattern matching and/or a pattern recognition can be performed in order to determine the delivery of the medicament.

In an embodiment, the device includes a pressure sensor for determining delivery of the adjusted dosage of the medicament.

The device can be designed to be mounted to the dosing adjusting means and/or to the delivery means of an insulin pen. Alternatively, the device can be designed to be mounted to a housing of the insulin pen, for example in the form of a bracket. Generally, when the device is mounted to the dosing adjusting means and/or the delivery means of the insulin pen, the quality of the signal generated by the motion sensing unit may be better than when the device is mounted to the housing of the insulin pen, because of the absorption or damping effect of the housing.

In an embodiment, the analyser is configured to determine orientation of the insulin pen and to generate protocol data distinguishing priming of the injection pen from delivery of the medicament. The gyro signal and/or the acceleration signal can indicate that a patient holds the injection pen in an upright position indicating that the patient performs a priming. The gyro signal and/or the acceleration signal can indicate that a patient holds the injection pen in a downward position indicating that the patient performs a delivery of the medicament. In the upright position, the needle of the injection pen is at the top. In the downward position, the needle of the injection pen is at the bottom. In the upright position and the downward position, the injection pen can be aligned to a vertical reference line within an angle of about 0° to 30°, for example.

In an embodiment, the analyser is configured to generate protocol data in accordance to the determination of the orientation of the injection pen during delivery of the medicament, of the velocity of the delivery of the medicament, and/or of the time period between delivery of the medicament and retraction of the injection pen. If orientation of the injection pen indicates that the injection pen is held in a position adapted for delivery of the medicament, protocol data can include data reflecting that the injection is held in a position adapted for delivery of the medicament. If velocity of the delivery of the medicament indicates that delivery of the medicament is performed sufficiently slow, protocol data can include data reflecting that delivery of the medicament is performed sufficiently slow, indicating that the medicament has been delivered properly. If velocity of the delivery of the medicament indicates that delivery of the medicament is performed too fast, protocol data can include data reflecting that delivery of the medicament is performed too fast, indicating that the medicament has not been properly delivered. If the time period between delivery of the medicament and retraction of the injection pen is sufficiently long, protocol data can include data indicating that the time period between delivery and retraction is sufficiently long, indicating that the medicament has been delivered properly. If the time period between delivery of the medicament and retraction of the injection pen is too short, protocol data can include data reflecting that the time period between delivery and retraction is too short, indicating that the medicament has not been properly delivered.

In an embodiment, the analyser is configured to determine a switch motion sequence and to switch the device from a low energy mode into a high energy mode upon detection of the switch motion sequence. Thus, a wake-up function is provided. The switch motion sequence can include a shaking of the injection pen, a sequence of particular positions of the injection pen with respect to ground, etc. In an embodiment, wake-up is provided on the basis of a mechanical switch or a proximity sensor.

In an embodiment, the analyser is configured to determine one or more predefined motion sequences and to include one or more predefined data elements into the generated protocol data upon detection of the one or more predefined motion sequences. For example, a motion for a downward position into a upward position and a shaking in the upward position can define that the patient realizes that a portion of the medicament has not been properly delivered. In this case, the analyser can be configured to include data into the generated protocol data reflecting that a portion of the medicament has not been properly delivered. The one or more predefined motion sequences can relate user defined gestures, wherein for each gesture the analyser can be configured to include data into the generated protocol data related to the particular gesture.

In an embodiment, the analyser is configured to analyse generated protocol data and to determine a future adjusted dosage of the medicament and a future delivery of the adjusted dosage of the medicament. The analyser can be configured to store user data defining characteristics of the patient, such as age, weight, etc. and to determine a future dosage of the medicament based on user data. In accordance to the future delivery of the medicament, the analyser can be configured to activate a user interface of the device, to transmit a message to a remote device, etc.

In an embodiment, the device is further configured to receive measurement data of a blood glucose level of a patient. Measurement data can be received through a communication interface, a user interface, etc. Measurement data can be based on a test-strip. Measurement data can be evaluated in connection of a humidity sensor and/or a temperature sensor included in the device.

Besides an inventive device for generating protocol data for an injection pen, the invention relates to an injection pen comprising the inventive device for generating protocol data for an injection pen. In an embodiment, the inventive device is fixedly mounted to the injection pen. The inventive device can be fixedly mounted to a dosing adjusting means of the injection pen and/or a delivery means of the injection pen.

BRIEF DESCRIPTION OF THE DRAWINGS

The herein described invention will be more fully understood from the detailed description given herein below and the accompanying drawings which should not be considered limiting to the invention described in the appended claims. The drawings are showing:

FIG. 1 illustrates schematically an injection pen having mounted a device for generating protocol data for the injection pen;

FIG. 2a illustrates schematically a side view of the device for generating protocol data of the injection pen;

FIG. 2b illustrates schematically a top view of the device for generating protocol data of the injection pen;

FIG. 3a illustrates schematically a perspective view of a front view of the device for generating protocol data of an injection pen;

FIG. 3b illustrates schematically a perspective view of a back view of the device for generating protocol data of an injection pen;

FIG. 4 illustrates schematically rotation of the device for generating protocol data of an injection pen;

FIG. 5 illustrates schematically an acceleration signal of the rotation of the device versus time;

FIG. 6 illustrates schematically the velocity signal and the integrated velocity signal of the rotation of the device versus time;

MODE(S) FOR CARRYING OUT THE INVENTION

Figure 7:
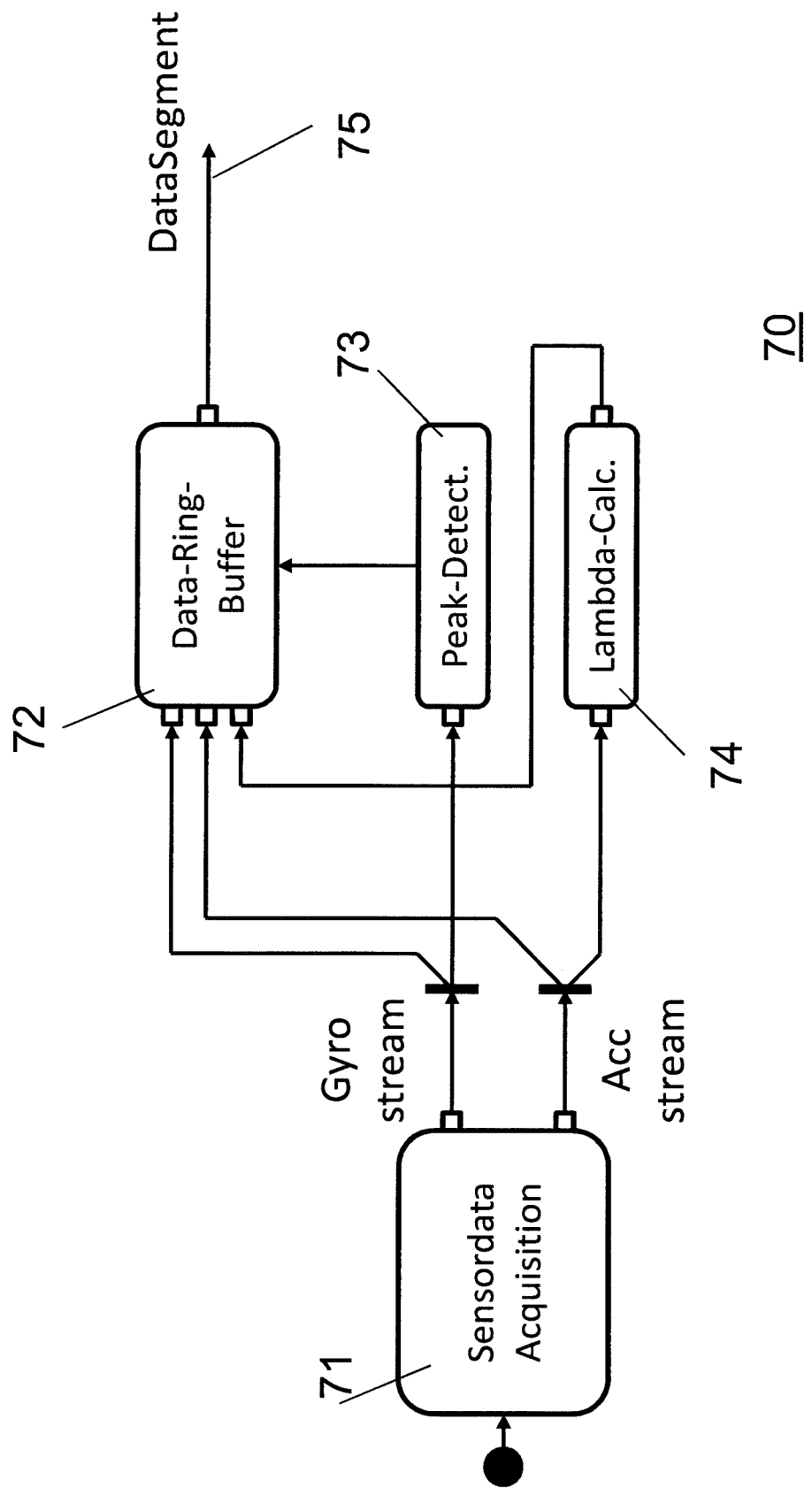
FIG. 7 illustrates schematically a pre-processing block configured to acquire a gyro signal and an acceleration signal and to provide data segments according to a peak detection.

FIG. 1 illustrates schematically an injection pen 2 having mounted a device 1 for generating protocol data for the injection pen 2. The injection pen 2 includes a medicament, such as insulin, for delivery to a patient via a needle (not shown in FIG. 1) of the injection pen 2. The injection pen 2 includes a dosing adjusting means (only partially shown as indicated by a dosage scale 21 in FIG. 1) for adjusting a dosage of the medicament and a delivery means (not shown in FIG. 1) for delivery of the adjusted medicament. In FIG. 1, a dosage scale 21 of the injection pen 2 is shown, which is a part of the dosing adjusting means.

The device 1 for generating protocol data is fixedly or releasably mounted on the injection pen 2. The device 1 includes a display of a user interface 11 which displays protocol data of the last injection performed with the injection pen 2, indicated by the string "6E", and the time since the last delivery of the medicament, indicated by the string "2h 30m".

The injection pen 2 has essentially a cylindrical shape and defines an axis of rotation. The device 1 for generating protocol data for the injection pen 2 is mounted to the dosage adjusting means 22 (only partially shown as indicated by a dosage scale 21 in FIG. 1) and the delivery means 23 (not shown in FIG. 1). A patient adjusts the dosage of the medicament by rotating the device 1 relative to the injection pen 2 about the axis of rotation. The adjusted dosage is displayed on the dosage scale 21. The patient delivers the dosage of the medicament by pushing the device 1 towards the injection pen 2, thereby activating the delivery means 23 (not shown in FIG. 1) of the injection pen 2.

FIG. 2a illustrates schematically a side view of the injection pen 2 having mounted the device 1 for generating protocol data of the injection pen 2. FIG. 2b illustrates schematically a top view of the device 1 for generating protocol data of the injection pen 2.

As illustrated in FIG. 2a, the device 1 includes an energy store 12, a motion sensing unit 13, a signal processing unit 14, a communication interface 15, and a user interface 16. The device 1 is mounted to the dosing adjusting means 22 of the injection pen 2. The device 1 is also mounted to the delivery means 23 of the injection pen 2. The signal processing unit 14 implements an analyser.

The indicated by arrow a2, the device 1 is rotatable about an axis of rotation defined by the cylindrical injection pen 2. Moreover, as indicated by arrow a3 the device 1 is pushable towards the injection pen 2. By rotating the device 1, the patient can adjust a dosage of the medicament, wherein rotation of the device 1 is transmitted to a rotation of the dosage adjusting means 22 of the injection pen 2. By pushing the device 1 towards the injection pen 2, the patient can initiate or perform delivery of the medicament, wherein the push movement of the device 1 is transmitted to a push movement of the delivery means 23 of the injection pen 2.

The injection pen 2 can be a commercially available injection pen designed for use without the device 1 for generating protocol data. The device 1 can comprise a mounting arrangement which fits a wide variety of commercially available injection pens 2. The mounting arrangement can include exchangeable adapters, each adapter being designed for mounting the device 1 to a particular type of a commercially available injection pen 2.

FIG. 2b illustrates schematically a top view of the device 1 for generating protocol data of the injection pen 2. FIG. 2b illustrates schematically the display of a user interface 11 of the device 1 and a housing of the device 1.

The user interface 11 of the device 1 can include an OLED display (OLED: Organic Light Emitting Diode), a TFT display (TFT: Thin-Film Transistor), a touchscreen, etc. The energy store 12 of the device 1 can include a battery, an accumulator, etc. The motion sensing unit 13 of the device 1 can include a MPU 9250 device from InvenSense® or another motion sensing unit. The signal processing unit 14, which implements the analyser, can include a LPC54102SMD microprocessor from NXP® or another signal processing unit. The communication interface 15 can include a Bluetooth interface or a Bluetooth Low Energy interface.

FIG. 3a illustrates schematically a perspective view of a front view of the device 1 for generating protocol data of an injection pen 2. The front view illustrates a display of a user interface 11 of the device 1.

FIG. 3b illustrates schematically a back view of the device 1 for generating protocol data of an injection pen 2. The back view illustrates a mounting arrangement 19 of the device 1. The mounting arrangement 19 is configured to mount the device on dosage adjusting means 22 and/or delivery means 23 of an injection pen 2.

FIG. 4 illustrates schematically rotation of the device 1 for generating protocol data of an injection pen 2. Rotation can occur about an axis of rotation of the injection pen 2. The analyser implemented by the signal processing unit 14 can be configured, based on signals received from the motion sensing unit 13, to analyse rotation based on a velocity of rotation of the device 1 and/or based on an acceleration of rotation of the device 1. Typically, the dosage adjusting means 22 of an injection pen 2 include a snap locking mechanism. The snap locking mechanism can provide steps of 18°, for example, such that a full rotation of the device 1 respectively of the dosage adjusting means 22 corresponds to twenty steps. With regard to the velocity of rotation, after each step, i.e. upon release of the snap locking mechanism, the velocity of rotation increases rapidly for a short time. With regard to the acceleration of the velocity of rotation, after each step, the acceleration increases rapidly for a short time as well.

FIG. 5 illustrates schematically an acceleration signal of the rotation of the device 1. Clearly, each step of rotation of the device 1 can be identified based on the acceleration signal. The acceleration signal can be combined with a velocity signal (not shown in FIG. 5) in order to identify steps of rotation of the device 1 respectively of the dosage adjusting means 22.

FIG. 6 illustrates schematically the velocity signal of the rotation of the device 1 versus time. A plurality of maxima is shown, wherein each maxima is followed by a minimum.

FIG. 5 illustrates nine maxima and nine minima, indicating that the device 1 has been rotated by nine snaps of the dosage adjusting means 22 of the injection pen 2.

FIG. 6 also illustrates schematically the integrated velocity signal of the rotation of the device 1 versus time. Nine steps are shown, wherein each step indicates that the device 1 has been rotated by a snap of the dosage adjusting means 22 of the injection pen 2.

FIG. 7 illustrates schematically a pre-processing block 70 configured to acquire a gyro signal and an acceleration signal and to provide data segments 75 according to a peak detection. The pre-processing block 70 includes a sensor acquisition block 71 which is connected to a gyroscope and to an accelerometer and which provides a gyro signal stream and an acceleration signal stream. The gyro signal and the acceleration signal are transmitted to a data ring buffer 72. The gyro signal is also transmitted to a peak detection block 73, which provides a peak detection to the data ring buffer 72. The acceleration signal is also transmitted to a lambda calculation block 74, which calculates lambda data related to an angle which reflects the projection of the gravitation vector onto a plane of rotation. The lambda data is transmitted to the data ring buffer 72. The data ring buffer 72 provides the data segments 75 in accordance to the peak detection of the peak detection block 73 such data is segmented into data segments which potentially include relevant data, such as data related to the dosage adjusting means 22 and/or of the delivery means 23 of the injection pen 2, for example corresponding to one or more steps of a snap locking mechanism.

Figure 8:
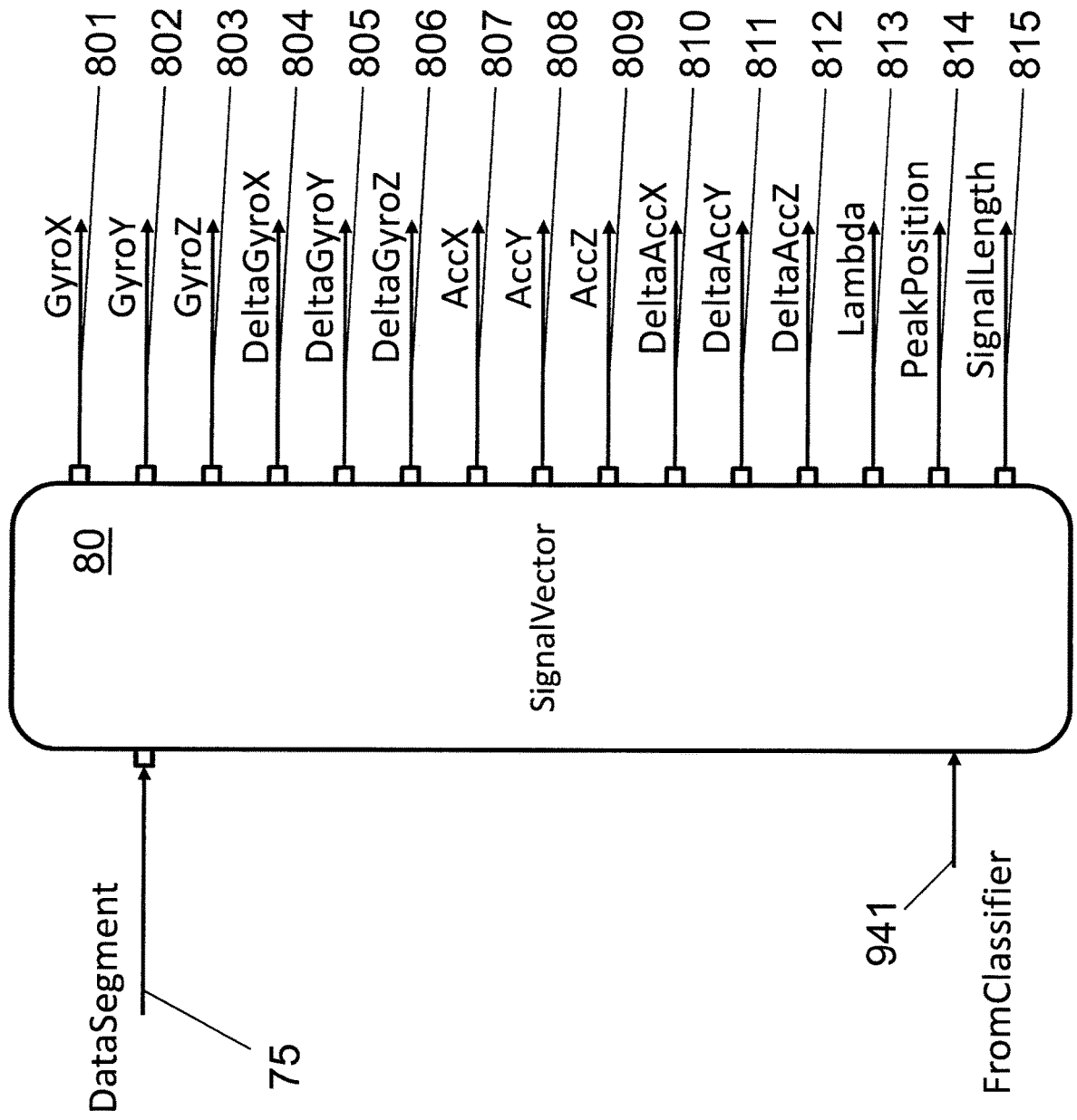
FIG. 8 illustrates schematically a signal vector block configured to receive data segments from the pre-processing block and to provide three-dimensional gyro and acceleration signals, derivatives with respect to time therefrom, a lambda signal, a peak position, and a signal length.

FIG. 8 illustrates schematically a signal vector block 80 configured to receive data segments 75 from the pre-processing block 70 and to provide three-dimensional gyro and acceleration signals, derivatives with respect to time therefrom, a lambda signal, a peak position, and a signal length. The signal vector includes: the signal GyroX 801 which reflects a component with respect to an x-axis of a gyroscope; the signal GyroY 802 which reflects a component with respect to an y-axis of a gyroscope; the signal GyroZ 803 which reflects a component with respect to a z-axis of a gyroscope; the signal DeltaGyroX 804 which reflects the derivation with respect to time of a component with respect to an x-axis of a gyroscope; the signal DeltaGyroY 805 which reflects the derivation with respect to time of a component with respect to an y-axis of a gyroscope; the signal DeltaGyroZ 806 which reflects the derivation with respect to time of a component with respect to a z-axis of a gyroscope; the signal AccX 807 which reflects a component with respect to an x-axis of an accelerometer; the signal AccY 808 which reflects a component with respect to an y-axis of an accelerometer; the signal AccZ 809 which reflects a component with respect to a z-axis of an accelerometer; the signal DeltaAccX 810 which reflects a derivative with respect to time of a component with respect to an x-axis of an accelerometer; the signal DeltaAccY 811 which reflects a derivative with respect to time of a component with respect to an y-axis of an accelerometer; the signal DeltaAccZ 812 which reflects a derivative with respect to time of a component with respect to a z-axis of an accelerometer; the signal Lambda 813 which reflects the lambda signal as described above; the peak position 814 which reflects the position of the detected peak as described above; and the signal length 815 which reflects the length of the signals provided by the signal vector block 80.

Figure 9:
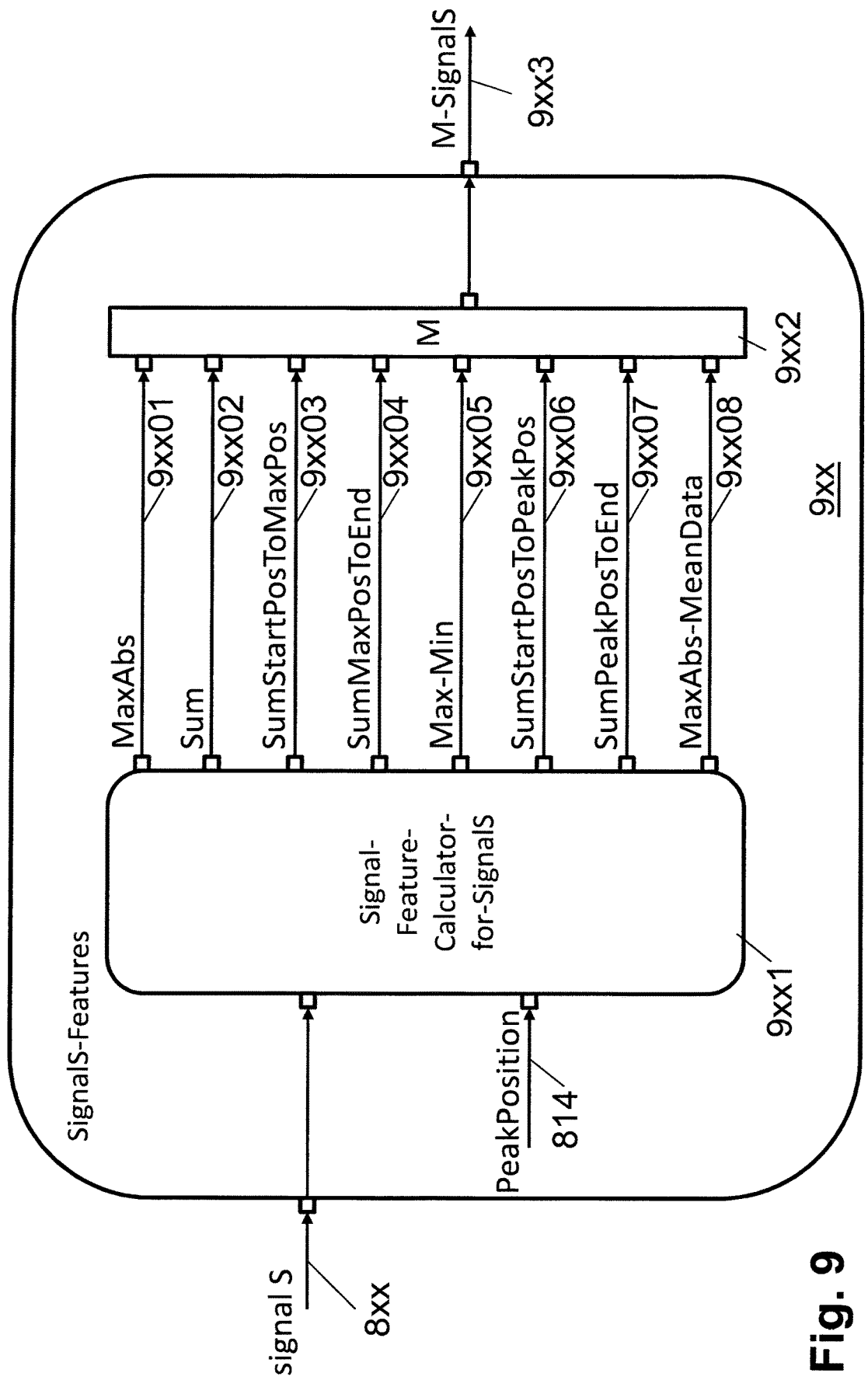
FIG. 9 illustrates schematically a feature calculator configured to receive a signal from the signal vector block and to provide signal features.

FIG. 9 illustrates schematically a feature calculator 9$xx$ configured to receive a signal S 8$xx$ and to provide signal features M-S 9$xx$3. In particular, the signal S 8$xx$ is one of the signals provided by the signal vector block 80. The feature calculator 9$xx$ includes a signal feature calculator 9$xx$1 and a feature assembler 9$xx$2. The signal feature calculator 9$xx$1 receives the signal S and the peak position 814 provided by the signal vector block 80. The signal feature calculator 9$xx$1 calculates the following features: MaxAbs 9$xx$01 is the absolute maximum value of a segment; Sum 9$xx$02 is the sum of the signal values of a segment; SumStartPosToMaxPos 9$xx$03 is the sum of the signal values from the start of the segment to the position of the absolute maximum value of the segment MaxAbs 9$xx$01; SumMaxPosToEnd 9$xx$04 is the sum of the signal values from the position of the absolute maximum value of the segment MaxAbs 9$xx$01 to the end of the segment; Max-Min 9$xx$05 is the difference between the maximal value minus the minimum value and reflects the signal swing; SumStartPosToPeakPos 9$xx$06 is the sum of the signal values from the start of the segment to the peak position in the segment; SumPeakPosToEnd 9$xx$07 is the sum of the signal values from the peak position in the segment to the end of the segment; and MaxAbs-MeanData 9$xx$08 is the difference between the absolute maximum value of a segment MaxAbs 9$xx$01 minus the mean value of the signal values of the segment. As illustrated in FIG. 9, the signal features calculated by the signal feature calculator 9$xx$1 are transmitted to the feature assembler 9$xx$2, which provides the signal features M-SignalS 9$xx$3.

Figure 10:
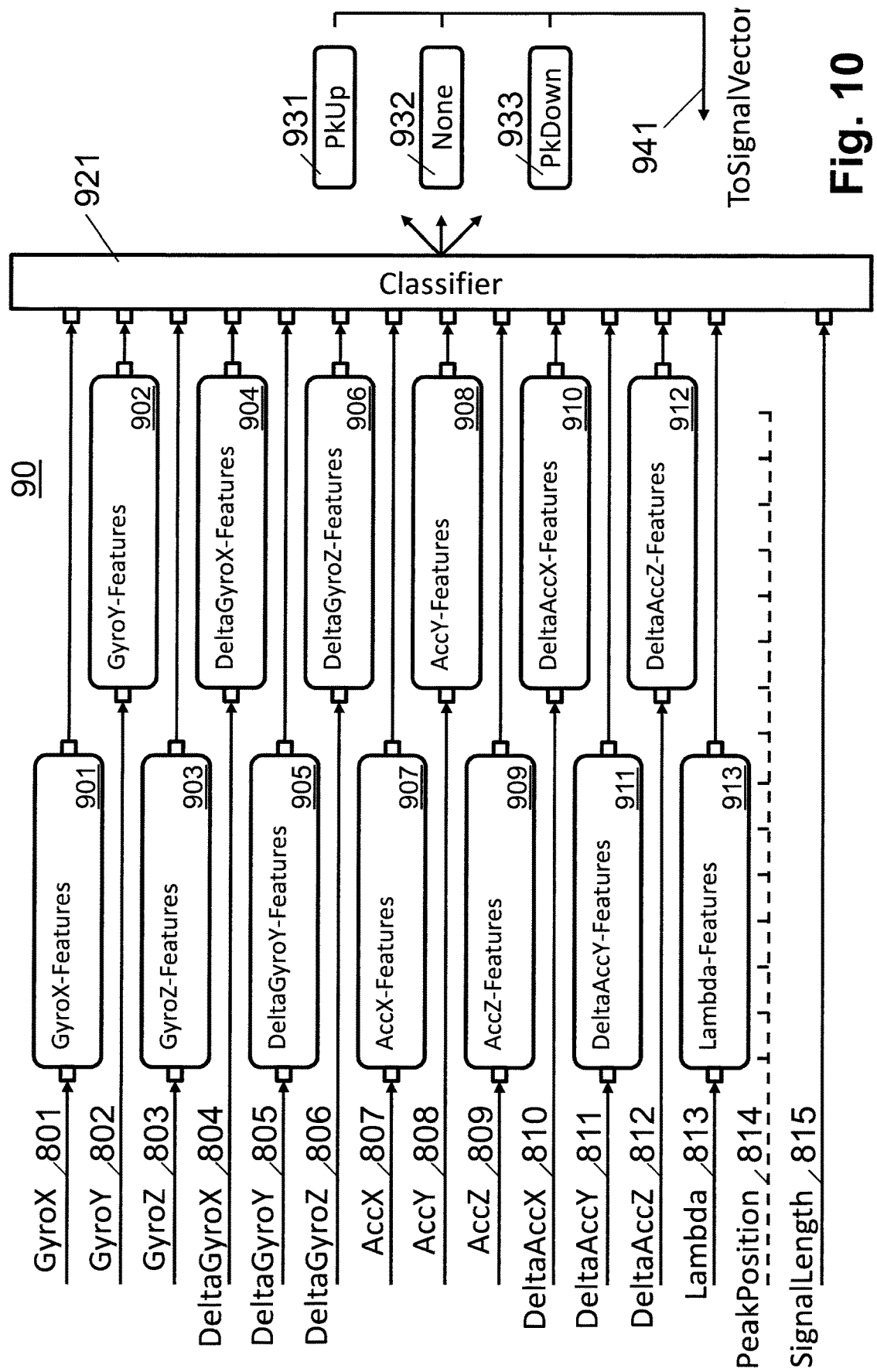
FIG. 10 illustrates schematically a plurality of feature calculators connected to a classifier for performing a classification on the basis of the signals provided by the signal vector block.

FIG. 10 illustrates schematically a plurality of feature calculators 901, 902, . . . 913 connected to a classifier 921 for performing a classification on the basis of the signals provided by the signal vector block. Each of the feature calculators 901, 902, . . . 913 receives one of a subset of signals 801, 802, . . . 813 provided by the signal vector block 80, calculates signal features as illustrated in FIG. 9 and transmits the signal features to the classifier 921. Each of the feature calculators 901, 902, . . . 913 receives the peak position 814 provided by the signal vector block 80. Additionally, the classifier 921 can receive the signal length 815 provided by the signal vector block 80. Additionally, the classifier 921 can receive a local peak position of the detected segment. The feature calculators 901, 902, . . . 913 transmit the following features to the classifier 921: the feature calculator 901 receives the GyroX 801 signal and provides GyroX features to the classifier 921; the feature calculator 902 receives the GyroY 802 signal and provides GyroY features to the classifier 921; the feature calculator 903 receives the GyroZ 803 signal and provides GyroZ features to the classifier 921; the feature calculator 904 receives the DeltaGyroX 804 signal and provides DeltaGyroX features to the classifier 921; the feature calculator 905 receives the DeltaGyroY 805 signal and provides DeltaGyroY features to the classifier 921; the feature calculator 906 receives the DeltaGyroZ 806 signal and provides DeltaGyroZ features to the classifier 921; the feature calculator 907 receives the AccX 807 signal and provides AccX features to the classifier 921; the feature calculator 908 receives the AccY 808 signal and provides AccY features to the classifier 921; the feature calculator 909 receives the AccZ 809 signal and provides AccZ features to the classifier 921; the feature calculator 910 receives the DeltaAccX 810 signal and provides DeltaAccX features to the classifier 921; the feature calculator 911 receives the DeltaAccY 811 signal and provides DeltaAccY features to the classifier 921; the feature calculator 912 receives the DeltaAccZ 812 signal and provides DeltaAccZ features to the classifier 921; and the feature calculator 913 receives the Lambda 813 signal and provides Lambda features to the classifier 921.

In an embodiment, the classifier 921 includes a random forest classifier. In an embodiment, the classifier 921 includes a support vector machine. The classifiers provides the following outputs: PkUp 931 if the gyro signal and the acceleration signal reflect that the patient manipulated the dosage adjusting means 22 of the injection pen 2 such that the dosage was increased, in particular by one step of a snap locking mechanism; PkDown 933 if the gyro signal and the acceleration signal reflect that the patient manipulated the dosage adjusting means 22 of the injection pen 2 such that the dosage was decreased, in particular by one step of a snap locking mechanism; None 932 if the gyro signal and the acceleration signal do not reflect that the patient manipulated the dosage adjusting means 22 of the injection pen 2, in particular neither to increase the dosage nor to decrease the dosage. As illustrated in FIG. 9, a feedback ToSignalVector 941 to the signal vector block 80 can be provided.

Figure 11:
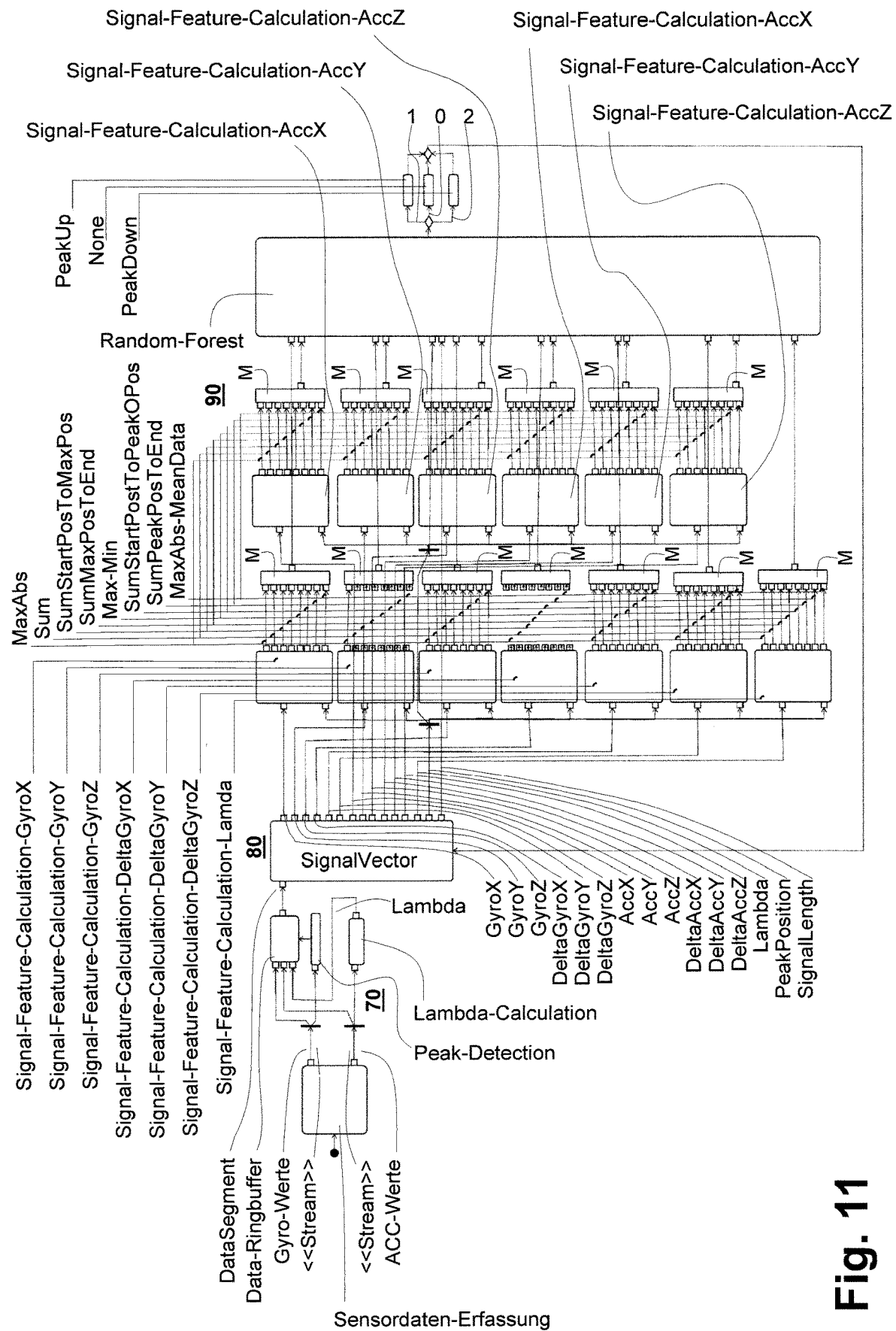
FIG. 11 illustrates schematically an algorithm in accordance to FIGS. 7-10 for acquiring gyro and acceleration signals and for detecting if a user has performed an up or a down manipulation.

FIG. 11 illustrates schematically an algorithm in accordance to FIGS. 7-10 for acquiring gyro and acceleration signals and for detecting if a user has performed an up or a down manipulation. FIG. 11 includes the pre-processing block 70 of FIG. 7. FIG. 11 includes the signal vector block 80 of FIG. 8. The pre-processing block 70 is connected via data segments 75 to the signal vector block 80. FIG. 11 includes a plurality of feature calculators 901, 902, . . . 913 of FIG. 10. The signal vector block 80 is connected via signals 801, 802, . . . 813 provided by the signal vector block 80 to the feature calculators 901, 902, . . . 913. The feature calculators 901, 902, . . . 913 each are embodied as illustrated in FIG. 9.

Further, the disclosure comprises embodiments according to the following clauses:

Clause 1. A device for generating protocol data for an injection pen, wherein the device comprises a motion sensing unit including one or more of a gyroscope and an accelerometer, and wherein the device comprises a signal processing unit which is configured to analyse one or more signals of the motion sensing unit in order to generate protocol data reflecting at least an adjusted dosage of a medicament and delivery of the adjusted dosage of the medicament.

Clause 2. The device according to clause 1, further comprising a communication interface for transmitting generated protocol data to an external protocol data recording device.

Clause 3. The device according to clause 1 or 2, wherein the signal processing unit is configured to generate protocol data having included a time stamp.

Clause 4. The device according to one of clauses 1 to 3, further comprising a mounting arrangement configured to detachably mount the device to the injection pen.

Clause 5. The device according to one of clauses 1 to 4, further comprising a user interface having one or more of a user output device and a user input device.

Clause 6. The device according to one of clauses 1 to 5, wherein device is configured to generate protocol data on the basis of one or more of an angular velocity and a derivative of the angular velocity of a dosing adjusting means of the injection pen.

Clause 7. The device according to one of clauses 1 to 6, wherein the device is configured to generate protocol data on the basis of one or more of an acceleration and a derivative of the acceleration of a delivery means of the injection pen.

Clause 8. The device according to one of clauses 1 to 7, wherein the signal processing unit is configured to determine orientation of the insulin pen and to generate protocol data distinguishing priming of the injection pen from delivery of the medicament.

Clause 9. The device according to one of clauses 1 to 8, wherein the signal processing unit is configured to generate protocol data in accordance to the determination of one or more of: orientation of the injection pen during delivery of the medicament, velocity of the delivery of the medicament, and time period between delivery of the medicament and retraction of the injection pen.

Clause 10. The device according to one of clauses 1 to 9, wherein the signal processing unit is configured to determine a switch motion sequence and to switch the device from a low energy mode into a high energy mode upon detection of the switch motion sequence.

Clause 11. The device according to one of clauses 1 to 10, wherein the signal processing unit is configured to determine one or more predefined motion sequences and to include one or more predefined data elements into the generated protocol data upon detection of the one or more predefined motion sequences.

Clause 12. The device according to one of clauses 1 to 11, wherein the signal processing unit is configured to analyse generated protocol data and to determine a future adjusted dosage of the medicament and a future delivery of the adjusted dosage of the medicament.

Clause 13. The device according to one of clauses 1 to 12, further configured to receive measurement data of a blood glucose level of a patient.

Clause 14. Injection pen comprising a device according to one of clauses 1 to 13.

Clause 15. Injection pen according to clause 14, wherein the device is fixedly mounted to the injection pen.

The invention claimed is:

1. A device for generating protocol data for an injection pen, wherein the device comprises a motion sensing unit including one or more of a gyroscope and an accelerometer in order to generate one or more of a gyro signal and an acceleration signal, and wherein the device comprises a signal processing unit which implements an analyser which is configured to analyse one or more of the gyro signal and the acceleration signal and to generate protocol data reflecting the amount of an adjusted dosage of a medicament.

2. The device according to claim 1, wherein the analyser is adaptable to different types of injection pens.

3. The device according to claim 1, wherein the analyser is configured to adapt itself to the corresponding injection pen.

4. The device according to claim 1, wherein the device includes a universal part which can be used with different types of injection pens and an adapter part which is designed to adapt the universal part to a particular type of injection pens.

5. The device according to claim 1, wherein the analyser is adaptable to an injection pen on the basis of a training sequence of a user.

6. The device according to claim 1, further comprising a communication interface for transmitting generated protocol data to an external protocol data recording device.

7. The device according to claim 1, wherein the analyser is configured to generate protocol data having included a time stamp.

8. The device according to claim 1, wherein the injection pen comprises a dosing adjusting means, the analyser being configured to analyse one or more of the gyro signal and the acceleration signal in order to determine one or more of an angular velocity and a derivative of the angular velocity of the dosing adjusting means and to generate protocol data on the basis of one or more of the angular velocity and the derivative of the angular velocity of the dosing adjusting means of the injection pen.

9. The device according to claim 1, wherein the analyser implements a data ring buffer which receives at least one of the gyro signal and the acceleration signal and which provides data segments in accordance to a peak detection in at least one of the gyro signal and the acceleration signal.

10. The device according to claim 1, wherein, for the analysis of at least one of the gyro signal and the acceleration signal, the analyser implements a signal vector which comprises one or more of the following components: an x-component of the gyro signal, a y-component of the gyro signal, a z-component of the gyro signal, a derivative with respect to time of an x-component of the gyro signal, a derivative with respect to time of an y-component of the gyro signal, a derivative with respect to time of an z-component of the gyro signal, an x-component of the acceleration signal, a y-component of the acceleration signal, a z-component of the acceleration signal, a derivative with respect to time of an x-component of the acceleration signal, a derivative with respect to time of an y-component of the acceleration signal, a derivative with respect to time of an z-component of the acceleration signal, a projection of the gyro signal, a peak position in the gyro signal, and a signal length of at least one of the gyro signal and the acceleration signal.

11. The device according to claim 1, wherein, for the analysis of at least one of the gyro signal and the acceleration signal, the analyser implements a feature calculation for one or more components of at least one of the gyro signal and the acceleration signal, wherein the feature calculation includes one or more of: the calculation of the absolute maximum value in a signal segment, the calculation of the sum of the values of a signal segment, the calculation of the sum from the start to an absolute maximum position of a signal segment, the calculation of the sum from an absolute maximum position to the end of a signal segment, the calculation of the sum from the start to a peak position of a signal segment, the calculation of the sum from a peak position to the end of a signal segment, the calculation of the difference between the maximum and the minimum of a signal segment, and the calculation of the difference between the absolute maximum and the mean of a signal segment.

12. The device according to claim 1, wherein, for the analysis of at least one of the gyro signal and the acceleration signal, the analyser implements a classifier in one or more of the following forms: a random forest classifier, and a support vector machine.

13. The device according to claim 1, wherein the analyser is configured to analyse one or more of the gyro signal and the acceleration signal in order to determine a motion sequence of the injection pen and to switch the device from a low energy mode into a high energy mode if the motion sequence corresponds to a predefined motion sequence.

14. An injection pen comprising a device according to claim 1.

15. The injection pen according to claim 14, wherein the device is fixedly mounted to the injection pen.

16. The device of claim 1, wherein both the gyro signal and the acceleration signal are generated and the signal processing unit analyses both signals to generate the protocol data.

17. The device of claim 1, wherein the signal processing unit analyses the one or more of the gyro signal and the acceleration signal to generate protocol data reflecting one or more of the fact of delivery and the time of delivery of the adjusted dosage.

18. The device of claim 17, wherein both of the gyro and acceleration signals are generated and the signal processing unit analyses both signals to generate the protocol data.

19. A device for generating protocol data for an injection pen, wherein the device comprises a motion sensing unit including one or more of a gyroscope and an accelerometer in order to generate one or more of a gyro signal and an acceleration signal, and wherein the device comprises a signal processing unit which implements an analyser which is configured to analyse one or more of the gyro signal and the acceleration signal and to generate protocol data reflecting the fact of delivery and/or the time of delivery of the adjusted dosage of a medicament.

20. The device of claim 19 in which the analyser is configured to generate protocol data reflecting the fact of delivery of the adjusted dosage of a medicament.

21. The device of claim 19 in which the analyser is configured to generate protocol data reflecting the time of delivery of the adjusted dosage of a medicament.

* * * * *